United States Patent [19]

Forestier et al.

[11] Patent Number: 5,106,611
[45] Date of Patent: Apr. 21, 1992

[54] USE OF MODIFIED DIORGANOPOLYSILOXANES AS ANTIOXIDANTS IN COSMETICS OR IN DERMATOLOGY

[75] Inventors: Serge Forestier, Claye-Souilly; Gerard Lang, Saint-Gratien; Hervé Richard, Paris, all of France

[73] Assignee: L'Oreal, Paris, France

[21] Appl. No.: 439,448

[22] Filed: Nov. 20, 1989

[30] Foreign Application Priority Data

Nov. 22, 1988 [LU] Luxembourg .................... 87395

[51] Int. Cl.$^5$ .................... A61K 7/021; A61K 7/06; A61K 7/48
[52] U.S. Cl. .................... 424/47; 424/63; 424/64; 424/70; 424/DIG. 5; 424/78.03; 252/134; 252/400.31; 514/772; 514/937; 514/938; 514/970; 514/844; 514/845; 514/846; 514/847; 514/944; 514/945
[58] Field of Search .................... 424/70, 63, 47, 78, 424/64; 514/772, 937, 938, 970, 844-847, 944, 945; 252/397, 398, 400.31, 134

[56] References Cited

U.S. PATENT DOCUMENTS

| | | | |
|---|---|---|---|
| 3,410,820 | 11/1968 | Harrod | 528/43 X |
| 3,579,467 | 5/1971 | Brown, Jr. | 252/46.3 |
| 3,586,705 | 6/1971 | Owen et al. | 252/400.31 X |
| 4,430,235 | 2/1984 | Chu et al. | 252/49.6 |
| 4,661,343 | 4/1987 | Zabotto et al. | 424/63 X |

FOREIGN PATENT DOCUMENTS

| | | |
|---|---|---|
| 1175266 | 12/1969 | United Kingdom . |
| 1203071 | 8/1970 | United Kingdom . |
| 1205222 | 9/1970 | United Kingdom . |

Primary Examiner—Thurman K. Page
Assistant Examiner—Susan S. Rucker
Attorney, Agent, or Firm—Marshall, O'Toole, Gerstein, Murray & Bicknell

[57] ABSTRACT

Use of modified diorganopolysiloxanes as antioxidants in cosmetics or in dermatology.

Use, as an antioxidizing agent in cosmetics or in dermatology, of diorganopolysiloxanes (i) of formula (I):

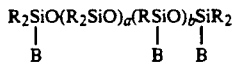

in which the symbols R denote alkyl or phenyl, B are chosen from the radicals R and A, a an integer chosen between 0 and 200 inclusive, b an integer chosen between 0 and 50 inclusive, and if b is equal to 0, at least one of the two symbols B is A, A is of formula:

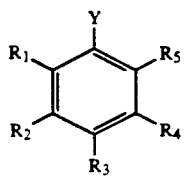

(III)

where:
$R_1$ denotes hydrogen or an alkyl,
$R_2$ denotes hydrogen, hydroxyl, alkyl or alkoxy,
$R_3$ denotes hydrogen, hydroxyl or alkyl,
$R_4$ denotes hydrogen or alkyl,
$R_5$ denotes hydrogen, hydroxyl or alkoxy,
Y denotes:

$$(O)_n-CH_2-CH(R_6)-CH_2-$$

where
$R_6$ denotes hydrogen or alkyl and n has the value of 0 or 1,
or (ii) of formula (II):

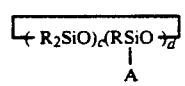

(II)

where
c is an integer between 1 and 20 inclusive,
d is an integer between 2 and 20 inclusive, and
c+d equal to or greater than 3.

7 Claims, No Drawings

USE OF MODIFIED DIORGANOPOLYSILOXANES AS ANTIOXIDANTS IN COSMETICS OR IN DERMATOLOGY

The present invention relates to the use of modified diorganopolysiloxanes as antioxidants in cosmetic or dermatological compositions and to the compositions containing these compounds.

It is known that fatty substances and certain active substances employed in cosmetic or dermatological compositions tend to oxidize, even at ambient temperature.

This oxidation causes them to acquire new, especially olfactive, properties which are undesirable when these substances are incorporated in cosmetic or dermatological compositions.

To avoid this oxidation, protective agents which act as antioxidants are generally employed. Di-tertbutylhydroxytoluene is commonly employed. However, the solubility of this compound in some fatty substances is limited.

The Applicant has discovered that certain diorganopolysiloxanes carrying alkylphenolic units have a substantially improved solubility in fatty substances and simultaneously exhibit excellent antioxidant properties in respect of the peroxidation of polyunsaturated lipids and also in respect of substances capable of undergoing heat- or photoinduced oxidation reactions (such as proteins, sugars, pigments, vitamins or polymers).

The Applicant has surprisingly found that the diorganopolysiloxanes in accordance with the present invention make it possible to ensure a better preservation of cosmetic or dermatological compositions comprising a fatty phase, by avoiding the development of rancidity of the unsaturated lipids present therein, and that they can also make it possible to avoid the oxidative degradation of active compounds present in these compositions, such as vitamin A or carotenoids.

In addition, the polymers in accordance with the present invention exhibit the advantage of not being absorbed by the skin.

The subject of the present invention is the use of diorganopolysiloxanes containing alkylphenolic units as antioxidant agents in cosmetic or dermatological compositions.

Another subject of the invention consists of cosmetic or dermatological compositions containing the diorganopolysiloxanes containing alkylphenolic units, defined below.

Further subjects in accordance with the invention will become appararent on reading the description.

The diorganopolysiloxanes employed as antioxidants in accordance with the present invention are chosen:

(i) from those of formula (I):

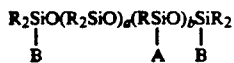

(I)

in which the symbols:

R, which are identical or different, are chosen from $C_1$-$C_{10}$ alkyl or phenyl radicals, at least 80 % of the number of the radicals R being methyl, B, which are identical or different, are chosen from the radicals R and the radical A, a is an integer chosen between 0 and 200 inclusive, b is an integer chosen between 0 and 50 inclusive, and if b is equal to 0 at least one of the two symbols B is A, A is a radical of formula

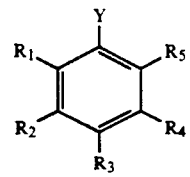

(III)

in which:

$R_1$ denotes a hydrogen atom or a $C_1$-$C_8$ linear or branched alkyl radical, $R_2$ denotes a hydrogen atom, a hydroxyl radical, a $C_1$-$C_8$ linear or branched alkyl radical or a $C_1$-$C_8$ linear or branched alkoxy radical, $R_3$ denotes a hydrogen atom, a hydroxyl radical or a $C_1$-$C_8$ linear or branched alkyl radical, $R_4$ denotes a hydrogen atom or a $C_1$-$C_8$ linear or branched alkyl radical, $R_5$ denotes a hydrogen atom, a hydroxyl radical or a $C_1$-$C_8$ linear or branched alkoxy radical, it being understood that at least one of the radicals $R_2$, $R_3$ and $R_5$ denotes a hydroxyl radical and that when $R_2$ is alkoxy and $R_3$ is hydroxy, at least one of the radicals $R_1$, $R_4$ and $R_5$ is other than a hydrogen atom, Y denotes a divalent radical:

$$-(O)_n-CH_2-CH(R_6)-CH_2-$$

in which:

$R_6$ denotes a hydrogen atom or a $C_1$-$C_4$ alkyl radical and n has the value of 0 or 1, (ii) and those of formula (II):

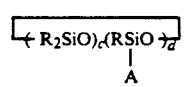

(II)

in which:

R and A have the same meanings as those shown in formula (I), c is an integer between 1 and 20 inclusive, d is an integer between 2 and 20 inclusive, and c+d is equal to or greater than 3.

Among the particularly preferred compounds employed in accordance with the invention there may be mentioned the random or block diorganopolysiloxanes of formulae (I) or (II) in which:

R is methyl,

B is methyl, a is between 5 and 20 inclusive, b is between 2 and 15 inclusive, c+d is between 3 and 10 inclusive, in radical A the alkyl radicals are chosen from methyl, ethyl, n-propyl, n-butyl, tert-butyl and 1,1,3,3-tetramethylbutyl radicals, the alkoxy radicals are preferably methoxy, and Y denotes a radical —$(CH_2)_3$— or —$O(CH_2)_3$—.

The diorganopolysiloxanes of formulae (I) or (II) are obtained by reacting a compound of formula:

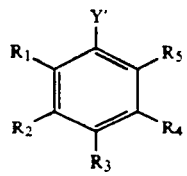

(VI)

in which $R_1$, $R_2$, $R_3$, $R_4$ and $R_5$ have the same meaning as shown in formula (III) above and Y' is the unsaturated radical of formula:

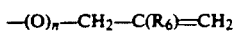

—(O)$_n$—CH$_2$—C(R$_6$)=CH$_2$ in which n and R: have the same meaning as in formula (III), with a copoly(organohydrodiorgano)siloxane, of formula:

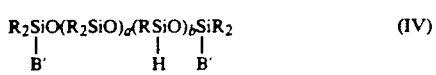

(IV)

in which R, a and b have the meaning shown above in formula (I) and the radicals $B_\prime$, which are identical or different, are chosen from the radicals R and a hydrogen atom and those of formula

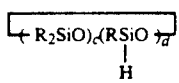

(V)

in which R, c and d have the meaning shown above in formula (II).

In what follows, this reaction will be called a hydrosilylation reaction.

The hydrosilylation reaction is carried out in the presence of a platinum-based catalyst such as platinum on charcoal, hexachloroplatinic acid, the product of reaction of hexachloroplatinic acid with an alcohol, an aldehyde or an ether, trimethylplatinum iodide, hexamethyldiplatinum or platinum complexed with derivatives containing unsaturations, for example olefins or vinylsiloxanes. These catalysts are described in U.S. Pat. No. 2,823,218, 3,220,972, 3,313,773, 3,159,601 and 3,159,662.

The hydrosilylation reaction may be optionally carried out in the presence of an inert volatile solvent, at a temperature between ambient temperature and 200° C., depending on the nature of the catalyst. The catalyst concentration is between $10^{-7}$ and $10^{-3}$, and preferably between $10^{-5}$ and $10^{-4}$ gram-atoms of platinum per mole of compound of formula (VI). The compound of formula (VI) is added slowly to the copoly(organohydrodiorgano)siloxane of formula (IV) or (V) containing the necessary quantity of catalyst, at a rate sufficient to keep the reaction mixture at a temperature which is generally between 50° and 120° C.

It is also possible to add the compound of formula (VI) and the copoly(organohydrodiorgano)siloxane of formula (IV) or (V) simultaneously to a suspension of catalyst in a solvent or else to add the copoly(organihydrodiorgano)siloxane of formula (IV) or (V) to the compound of formula (VI), optionally in solution in a solvent and containing the necessary quantity of catalyst. The reaction is carried out by employing stoichiometric proportions of the reactants (IV), (V) and (VI) or optionally a slight deficiency of reactant (VI) or of the copoly(organohydrodiorgan)siloxane of formula (IV) or (V).

Among the derivatives of formula (VI) which are defined above there may be mentioned more particularly:
4-allyl-2,6-di-tert-butylphenol,
2-allyl-4,6-di-tert-butylphenol,
2-allyl-4-methoxy-6-tert-butylphenol,
2-allyl-4-methyl-6-tert-butylphenol,
2-allyl-4-methyl-6-(1,1,3,3-tetramethylbutyl)phenol,
4-allyloxy-2,6-di-tert-butylphenol,
4-allyloxy-2-tert-butylphenol, and
2-allyl-5-tert-butylhydroquinone.

The derivatives of formula (VI) are known and can be prepared according to known methods.

For example, the derivatives of formula (VI) in which Y' denotes an unsaturated radical of formula (O)$_n$—CH$_2$—C(R$_6$)=CH$_2$, when n=1, can be obtained by reaction of an alkenyl halide of formula (VII) with a derivative of formula (VIII):

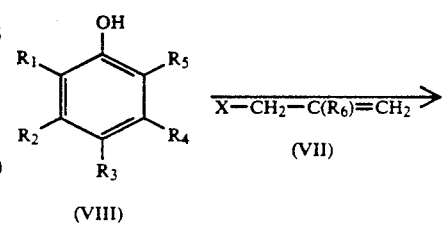

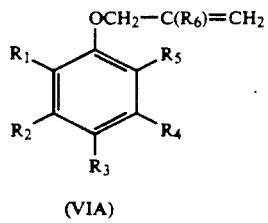

This reaction is carried out in the presence of a base in a solvent or a mixture of solvents, for example in the presence of an alkali metal carbonate in dimethylformamide or in the presence of an alkali metal hydroxide and of a phase transfer catalyst in a mixture of toluene and water, at a temperature between the ambient temperature and the boiling point of the solvent.

In compounds of formulae (VIA), (VII) and (VIII), $R_1$, $R_2$, $R_3$, $R_4$, $R_5$ and $R_6$ have the meanings shown above and X denotes a halogen atom, preferably a chlorine or bromine atom.

The derivatives of formula (VI) in which $R_3$=OH and Y' denotes an unsaturated radical of formula —(O)-$_n$—CH$_2$—C(R$_6$)=CH$_2$, when n=0, may be obtained by a Claisen rearrangement of a compound of formula (IX) according to the reaction scheme below:

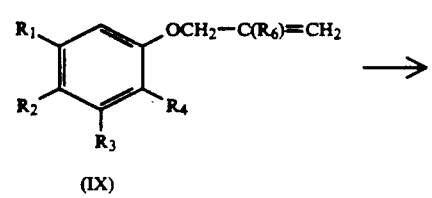

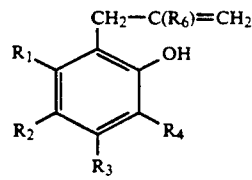

(VIB)

This rearrangement can be carried out in the conditions described by Tarbell (Organic Reactions, vol. 2, John Wiley, New York, 1944, page 1) by heating the compound of formula (IX) to at least approximately 170° C., optionally in the presence of a solvent.

The compound of formula (IX) can be obtained by reaction of an alkenyl halide of formula (VII) with a compound of formula (X):

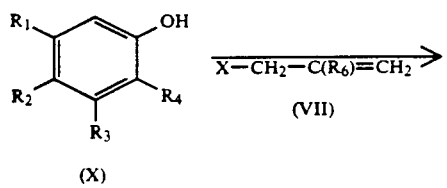

(X)  (VII)

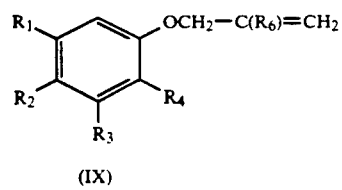

(IX)

This reaction is carried out in the presence of a base in a solvent or a mixture of solvents, for example in the presence of an alkali metal carbonate in dimethylformamide or in the presence of an alkali metal hydroxide and of a phase transfer catalyst in a mixture of toluene and water, at a temperature between the ambient temperature and the boiling point of the solvent. The compound of formula (X) can be prepared by known methods. In the compounds of formulae (VIB), (VII), (IX) and (X), $R_1$, $R_2$, $R_3$, $R_4$, $R_6$ and X have the meanings shown above.

The derivatives of formula (VI) in which $R_3$=OH, $R_1$=$R_5$=H, $R_2$ and $R_4$ denote a $C_1$-$C_8$ linear or branched alkyl radical and Y' denotes an unsaturated radical of formula —(O)$_n$—CH$_2$—C(R$_6$)=CH$_2$, when n=0, can be obtained by reaction of an alkenyl halide of formula (VII) with a derivative of formula (XI):

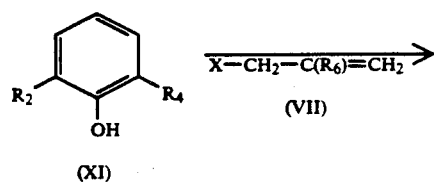

(XI)  (VII)

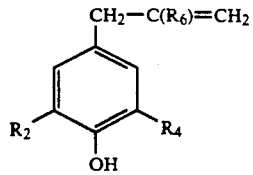

(VIC)

This reaction is carried out in the presence of a base in a solvent or a mixture of solvents, for example in the presence of an alkali metal alcoholate or carbonate in dimethylformamide or in the presence of an alkali metal hydroxide, optionally in the presence of a phase transfer catalyst in toluene, at a temperature between the ambient temperature and the boiling point of the solvent. The compounds of formula (XI) are known compounds.

The cosmetic or dermatological compositions in accordance with the invention are essentially characterized in that they contain, in a cosmetically or dermatologically acceptable medium containing a fatty phase of animal, plant or synthetic origin and/or an active substance susceptible to oxidation, at least one diorganopolysiloxane of formula (I) or (II) in concentrations of between 0.01 and 5 %, and preferably between 0.05 and 3 % by weight relative to the total weight of the composition.

The fatty substances employed in accordance with the present invention consist of unsaturated lipids of animal origin, such as lanolin, cetin (spermaceti), beeswax, perhydrosqualene, turtle oil, or of plant origin, such as olive oil, castor oil, avocado oil, sunflower oil, soya-bean oil, peanut oil, corn oil, karite-nut oil, sweet almond oil, sesame oil, blackcurrant oil, copra or cabbage palm oil, fats such as cocoa butter, waxes such as carnauba wax, montan wax, candelilla wax, essential fatty acids such as vitamin F and the essential oils present in perfumes, such as lemon or lavender oil.

The active substances employed in accordance with the present invention are chosen from those generally employed in the field of cosmetics or of dermatology, such as vitamin A, carotenoids, proteins, natural pigments, sugars and polymers.

These compositions may also contain thickeners, skin-compatible solvents such as $C_1$-$C_4$ lower alcohols like ethanol, polyalcohols such as propylene glycol, or any other suitable solvent, and softeners, superfattening agents, emollients, wetting agents, anionic, cationic, nonionic or amphoteric surfactants or mixtures thereof, sunscreens, dyes intended to colour the skin or the composition itself, and any other ingredient usually employed in cosmetic or dermatological compositions.

The cosmetic or dermatological compositions in accordance with the present invention are presented in the form of oily solutions, oil-in-water or water-in-oil emulsions (creams or milks), solid sticks, more or less thickened lotions, gels, pomades, saturated pads, aerosol sprays or foam, or soap tablets.

A preferred embodiment of the invention consists of lotions, creams and milks for facial care, body milks and creams, milks or creams for removing make-up, foundation creams, coloured creams, make-up bases, masks, lip rouges, mascaras, etc.

Another subject of the invention consists of a process of protection against the oxidation of oxidizable cosmetic or dermatological substances, characterized in that an effective quantity of at least one diorganopolysiloxane of formula (I) or (II) is incorporated into the said substances.

The examples which follow are used to illustrate the invention without, however, being of a limiting nature.

EXAMPLE 1

Preparation of a compound of general formula (I) in which $R=B=CH_3$, $a=b=6$, and A denotes a radical of formula (III) in which $R_1=R_5=H$, $R_2=R_4=$ tert-butyl, $R_3=OH$ and $Y=-(CH_2)_3-$.

A toluene solution (175 ml) of 4-allyl-2,6-di-tert-butylphenol (90 g, 365 meq) and of polymethylhydro(4-5-50%) dimethylsiloxane copolymer (Petrach Systems Inc., PS 122.5 54 g, 332 meq as SiH) is added dropwise over one hour 45 minutes to a suspension of 5% platinum on charcoal (520 mg) in dry toluene (25 ml) at 90°-100° C., under nitrogen and with stirring, while the temperature is maintained between 100° and 105° C. Stirring and refluxing are continued until the disappearance of the SiH groups (absence of a band at 2180 cm$^{-1}$ in the infrared), that is for 8 hours. The mixture is filtered through paper, the solid is rinsed with dichloromethane and the solvents are removed. The red-brown oil obtained (143.6 g) is chromatographed on silica gel 60. The excess olefin is removed by elution with a 20/80 dichloromethane/heptane mixture. Elution with pure dichloromethane enables the expected product to be obtained in the form of a thick pale-yellow oil (106 g, yield = 78%).

| $^1$H NMR spectrum (CDCl$_3$): | spectrum consistent with the formula |
|---|---|
| $^{29}$Si NMR spectrum (CDCl$_3$): | spectrum consistent with the formula. |

EXAMPLE 2

Preparation of a compound of general formula (I) in which $R=B=CH_3$, $a=b=6$, and A denotes a radical of formula (III) in which $R_1=R_3=H$, $R_2=R_4=$ tert-butyl, $R_5=OH$ and $Y=-(CH_2)_3-$.

1) Preparation of 2,4-di-tert-butylallyloxybenzene.

Sodium hydroxide pellets (20 g, 0.5 moles), water (25 g), toluene (50 ml) and tetrabutylammonium hydrogen sulphate (1 g) are added in succession into a reactor. They are heated to 50° C. with stirring and under nitrogen and a toluene solution (50 ml) of allyl bromide (16.5 g, 0.134 moles) and of 2,4-di-tert-butylphenol (25 g, 0.12 moles) is added over 45 minutes. The temperature rises progressively to 68° C. The materials are left at this temperature for 3 hours. Cooling is applied, 50 ml of water and 50 ml of toluene are added and the phases are separated. The toluene phase is washed with water and dried over sodium sulphate and the solvent is evaporated off to give an orange-coloured oil which is purified on a bed of silica gel 60 (eluent: heptane). 2,4-Di-tert-butylallyloxybenzene is obtained as a colourless liquid (23 g, yield = 78 %).

2) Preparation of 2-allyl-4,6-di-tert-butylphenol.

10 g of 2,4-di-tert-butylallyloxybenzene are heated under nitrogen to 245° C. for 45 minutes. The yellow crude oil is taken up in diisopropyl ether. The ether phase is washed with 3 % sodium hydroxide and then with water. After drying and evaporation of the solvent, the oil obtained (7.6 g) is chromatographed on silica gel 60 (eluent: 80/20 heptane/CH$_2$Cl$_2$). A pale-yellow oil of 2-allyl-4,6-di-tert-butylphenol is obtained (5.4 g, yield = 54 %).

3) Hydrosilylation reaction.

A toluene solution (10 ml) of 2-allyl-4,6-di-tert-butylphenol (4.3 g, 17.5 meq) and of polymethylhydro(45-50 %)dimethylsiloxane copolymer (Petrach Systems Inc., PS 122.5, 2.56 g, 16 meq as SiH) is added dropwise over 45 minutes to a suspension of 5 % platinum on charcoal (27 mg) in dry toluene (5 ml) at 90°-100° C., under nitrogen and with stirring, while the temperature is maintained between 100° and 105° C. Stirring and refluxing are continued until the disappearance of the SiH groups (absence of a band at 2180 cm$^{-1}$ in the infrared), that is for 8 hours. The mixture is filtered through paper and the solvent is removed. The orange-yellow oil obtained (6.8 g) is chromatographed on silica gel 60. The excess olefin is removed by elution with a 35/65 dichloromethane/heptane mixture. Elution with pure dichloromethane makes it then possible to obtain, after evaporation of the solvent, a thick pale-yellow oil (2.9 g, yield = 45 %).

| $^1$H NMR spectrum (CDCl$_3$) | spectrum consistent with the formula |
|---|---|
| $^{29}$Si NMR spectrum (CDCl$_3$) | spectrum consistent with the formula. |

| $^1$H NMR spectrum (CDCl$_3$): | spectrum consistent with the formula |
|---|---|
| $^{29}$Si NMR spectrum (CDCl$_3$): | spectrum consistent with the formula. |

EXAMPLE 3

Preparation of a compound of general formula (I) in which $R=B=CH_3$, $a=b=6$, and A denotes a radical of formula (III) in which $R_1=R_3=H$, $R_2=OCH_3$, $R_4=$ tert-butyl, $R_5=OH$ and $Y=-(CH_2)_3-$.

A toluene solution (30 ml) of 2-allyl-4-methoxy-6-tert-butylphenol (8.6 g, 39 meq) and of polymethylhydro(45-50 %)dimethylsiloxane copolymer (Petrarch Systems Inc., PS 122.5, 5.77 g, 35.5 meq as SiH) is added dropwise over 90 minutes to a suspension of 5 % platinum on charcoal (50 mg) in dry toluene (5 ml) at 90°-100° C., under nitrogen and with stirring, while the temperature is maintained between 100° and 105° C. Stirring and refluxing are continued until the disappearance of the SiH groups (absence of a band at 2180 cm$^{-1}$ in the infrared), that is for 8 hours. The mixture is filtered through paper, the solvent is removed and an orange-coloured oil is obtained, which is chromatographed on silica gel 60. The starting olefin is recovered by using a 20/80 dichloromethane/heptane mixture as eluent. On elution with pure dichloromethane and after evaporation of the solvent, the extracted product is obtained as a thick orange-coloured oil (12 g, yield = 88 %).

| $^1$H NMR spectrum (CDCl$_3$): | spectrum consistent with the formula |
|---|---|
| $^{29}$Si NMR spectrum (CDCl$_3$): | spectrum consistent with the |

EXAMPLE 4

Preparation of a compound of general formula (I) in which $R=B=CH_3$, $a=b=6$, and A denotes a radical of formula (III) in which $R_1=R_3=H$, $R_2=$methyl, $R_4=$tert-butyl, $R_5=OH$ and $Y=-(CH_2)_3-$.

A toluene solution (60 ml) of 2-allyl-4-methyl-6-tert-butylphenol (16.5 g, 81 meq) and of polymethylhydro(45-50 %)dimethylsiloxane copolymer (Petrarch Systems Inc., PS 122.5, 12.47 g, 76.8 meq as SiH) is added dropwise over 90 minutes to a suspension of 5 % platinum on charcoal (101 mg) in dry toluene (5 ml) at 90°-100° C., under nitrogen and with stirring, while the temperature is maintained between 100° and 105° C. Stirring and refluxing are continued until the disappearance of the SiH groups (absence of a band at 2180 cm$^{-1}$ in the infrared), that is for 8 hours. The mixture is filtered through paper, the solvent is removed and the material is washed twice with 70 % ethanol. The orange-yellow oil obtained is taken up in dichloromethane. The organic phase is dried over sodium sulphate and is filtered through a bed of silica gel 60. After evaporation of the solvent, the expected product is obtained as a thick orange-yellow oil (26 g, yield =92 %).

| $^1$H NMR spectrum (CDCl$_3$): | spectrum consistent with the formula |
|---|---|
| $^{29}$Si NMR spectrum (CDCl$_3$): | spectrum consistent with the formula. |

EXAMPLE 5

Preparation of a compound of general formula (I) in which $R=B=CH_3$, $a=b=6$, and A denotes a radical of formula (III) in which $R_1=R_2=R_5=H$, $R_4=$tert-butyl, $R_3=OH$ and $Y=-(O)-(CH_2)_3-$.

A toluene solution (15 ml) of 4-allyloxy-2-tert-butylphenol (2.1 g, 10 meq) and of polymethylhydro(45-50 %)dimethylsiloxane copolymer (Petrarch Systems Inc., PS 122.5, 1.49 g, 9.2 meq as SiH) is added dropwise over thirty minutes to a suspension of 5 % platinum on charcoal (15 mg) in dry toluene (5 ml) at 90°-100° C., under nitrogen and with stirring, while the temperature is maintained between 100° and 105° C. Stirring and refluxing are continued until the disappearance of the SiH groups (absence of a band at 2180 cm$^{-1}$ in the infrared), that is for 8 hours. The mixture is filtered through paper, the solvent is removed and the material is washed twice with 70 % ethanol. The pale-yellow oil obtained is taken up in chloroform. The organic phase is dried over sodium sulphate and is filtered through a bed of silica gel 60. After evaporation of the solvent, the expected product is obtained as a thick pale-yellow oil (1.4 g, yield 41 %).

| $^1$H NMR spectrum (CDCl$_3$): | spectrum consistent with the formula |
|---|---|
| $^{29}$Si NMR spectrum (CDCl$_3$): | spectrum consistent with the formula. |

EXAMPLE 6

Preparation of a compound of general formula (I) in which $R=B=CH_3$, $a=b=6$, and A denotes a radical of formula (III) in which $R_1=R_4=H$, $R_3=$tert-butyl, $R_2=R_5=OH$ and $Y=-(CH_2)_3-$.

A toluene solution (10 ml) of 2-allyl-5-tert-butylhydroquinone (1.45 g, 7 meq) and of polymethylhydro(45-50 %)dimethylsiloxane copolymer (Petrarch Systems Inc., PS 122.5, 1.03 g, 6.32 meq as SiH) is added dropwise over 90 minutes to a suspension of 5 % platinum on charcoal (12 mg) in dry toluene (5 ml) at 90°-100° C., under nitrogen and with stirring, while the temperature is maintained between 100° and 105° C. Stirring and refluxing are continued until the disappearance of the SiH groups (absence of a band at 2180 cm.: in the infrared), that is for 8 hours. The mixture is filtered through paper, the solvent is removed and the material is washed twice with 80 % ethanol. The pale-yellow oil obtained is taken up in dichloromethane. The organic phase is dried over sodium sulphate and is filtered through a bed of silica gel 60. After evaporation of the solvent, the expected product is obtained as a thick pale-yellow oil (1.5 g, yield =64 %).

| $^1$H NMR spectrum (CDCl$_3$): | spectrum consistent with the formula |
|---|---|
| $^{29}$Si NMR spectrum (CDCl$_3$): | spectrum consistent with the formula. |

EXAMPLE OF APPLICATION 1

| BODY MILK (W/O emulsion) | |
|---|---|
| Compound of Example 2 | 0.2 g |
| PEG 45/dodecylglycol copolymer of formula: | |

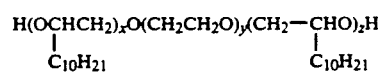

| where x = z = 11 and y = 45 | |
|---|---|
| sold by Akzo under the name Elfacos ST9 | 2.5 g |
| Mixture of diglycerol mono- and diester of oleic acid, sold by American Hoechst under the name Hostacerine DGO | 2.5 g |
| Montmorillonite modified with dimethyldialkyl-(hydrogenated tallow)ammonium groups, sold by NL Industries under the name Bentone 38 | 1.0 g |
| Volatile silicone | 8.0 g |
| Purcellin oil | 6.0 g |
| Sunflower oil | 6.0 g |
| Preservatives | 0.35 g |
| Glycerine | 5.0 g |
| Perfume | 0.2 g |
| Demineralized water q.s. | 100.0 g |

The compound of Example 2 can be replaced with the same quantity of compound of Example 5.

EXAMPLE OF APPLICATION 2

| COMPACT MAKEUP FOUNDATION | |
|---|---|
| Compound of Example 3 | 0.15 g |
| Isopropyl isostearate | 40.75 g |
| Sweet almond oil | 8.0 g |
| Pigments | 42.0 g |
| Ozokerite | 3.0 g |
| Silica | 1.0 g |
| Carnauba wax | 5.0 g |

-continued

| COMPACT MAKEUP FOUNDATION | |
|---|---|
| Propyl para-hydroxybenzoate | 0.1 g |

The compound of Example 3 can be replaced by the same quantity of compound of Example 6.

EXAMPLE OF APPLICATION 3

| LIP ROUGE | |
|---|---|
| Compound of Example 1 | 0.4 g |
| Ozokerite | 16.0 g |
| Microcrystalline wax | 6.0 g |
| Candelilla wax | 9.0 g |
| Sesame oil | 14.0 g |
| Castor oil | 6.0 g |
| Liquid lanolin | 8.0 g |
| Acetylated lanolin | 8.0 g |
| Talc | 5.0 g |
| Mica-titania | 10.0 g |
| DC - Red 7 Ca lake | 4.2 g |
| DC - Red 6 Ba lake | 2.3 g |
| FDC Yellow 5 | 0.8 g |
| Titanium dioxide | 2.5 g |
| Sunflower oil | 8.0 g |

Demonstration of the antioxidant power of the polysiloxane in the lip rouge:

The lip rouge base is heated in a bath thermostated at 120° C., with air bubbling at 30 ml/min. The gas stream is lead into a second receptacle containing water. The conductivity of this aqueous medium is followed; this increases with the appearance of secondary oxidation products (propionic and acetic acids, etc.). The measured induction time corresponds to the latency period observed before the exponential increase in conductivity.

In the case of lip rouge base without any antioxidant the induction time is 79 minutes.

In the case of the base of the Example of Application 3, the time is 490 minutes.

By way of comparison, when the polysiloxane of Example 1 is replaced with di-tert-butylhydroxytoluene (at an equivalent concentration of BHT units in the case of the polysiloxane), that is 0.2 % of BHT, the induction time is 225 minutes.

EXAMPLE OF APPLICATION 4

Demonstration of the antioxidant power of the compound of Example 4 with regard to vitamin F.

The following results are obtained by operating in the same manner as above, but heating vitamin F in a bath thermostated at 100° C. instead of 120° C.:
vitamin F alone: induction time = 20 minutes
vitamin F + 0.34 % of polysiloxane of Example 4: induction time = 303 minutes.

What is claimed is:

1. A cosmetic or dermatological composition comprising a cosmetically or dermatologically acceptable medium containing a fatty phase of animal, plant, or synthetic origin, or an active substance susceptible to oxidation, and as an antioxidant at least one diorganopolysiloxane having:

(a) the formula

(I)

in which:

R, which can be identical or different, are $C_1-C_{10}$ alkyl or phenyl radicals, at least 80% of the number of the radicals R being methyl, B, which can be identical or different, are selected from R and A, a is an integer between 0 and 200 inclusive, b is an integer between 0 and 50 inclusive, and if b is equal to 0, at least one of the two symbols B is A, A is a radical of formula:

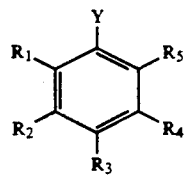
(III)

in which:

$R_1$ is hydrogen or $C_1-C_8$ linear or branched alkyl, $R_2$ is hydrogen, hydroxyl, $C_1-C_8$ linear or branched alkyl, or $C_1-C_8$ linear or branched alkoxy, $R_3$ is hydrogen, hydroxyl, or $C_1-C_8$ linear or branched alkyl, $R_4$ is hydrogen or $C_1-C_8$ linear or branched alkyl, $R_5$ is hydrogen or $C_1-C_8$ linear or branched alkoxy, at least one of the radicals $R_2$, $R_3$, and $R_5$ denoting hydroxyl, Y is a divalent radical of formula $$(O)_n-CH_2-CH(R_6)-CH_2-$$

in which:

$R_6$ is hydrogen or $C_1-C_4$ alkyl and an is 0 or 1, with the proviso that when n is 0, at least two of the radicals $R_1$, $R_2$, $R_3$, $R_4$, $R_5$ other than those of $R_2$, $R_3$, or $R_5$ which denote hydroxyl are different from hydrogen, or, (b) the formula:

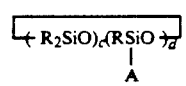
(II)

in which:

R and A have the same meanings as those shown in formula (I), c is an integer between 1 and 20 inclusive, d is an integer between 2 and 20 inclusive, and c+d is equal to or greater than 3, said antioxidant being present in an amount effective to prevent oxidation of said fatty phase or said active substance.

2. A composition according to claim 1, in which said diorganopolysiloxane is a random or block polymer of formula (I) or (II), in which:

R is methyl;

B is methyl, a is between 5 and 20 inclusive, b is between 2 and 15 inclusive, c+d is between 3 and 10 inclusive, and in the radical A the alkyls are selected from the group consisting of methyl, ethyl, n-propyl, n-butyl, tert-butyl and 1,1,3,3-tetramethylbutyl groups, the alkoxy radicals are methoxy, and Y is —(CH$_2$)$_3$— or —O(CH$_3$)$_3$—.

3. A composition according to claim 1, containing said diorganopolysiloxane in a concentration of 0.01 to 5% by weight based on the total weight of the composition.

4. A composition according to claim 1, containing said diorganopolysiloxane in a concentration of 0.05 to 3% by weight based on the total weight of the composition.

5. A composition according to claim 1 in a form selected from the group consisting of oily solutions, oil-in-water or water-in-oil emulsions, creams or milks, solid sticks, thickened lotions, gels, pomades, saturated pads, aerosol sprays, foam, and soap tablets.

6. A composition according to claim 1 which additionally contains an additive selected from the group consisting of softening agents, thickeners, sequestrants, emollients, wetting agents, perfumes, colorants, anionic, cationic, nonionic, or amphoteric surface-active agents or mixtures thereof and sunscreens.

7. A method for protecting an oxidizable cosmetic or dermatological substance against oxidation, comprising incorporating into said substance at least one diorganopolysiloxane having (a) the formula

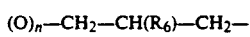
$$R_2SiO(R_2SiO)_a(RSiO)_bSiR_2 \quad (I)$$
$$\phantom{R_2SiO(}B\phantom{R_2SiO)_a}A\phantom{(R}B$$

in which:

R, which can be identical or different, are $C_1$–$C_{10}$ alkyl or phenyl radicals, at least 80% of the number of the radicals R being methyl, B, which can be identical or different, are selected from R and A, a is an integer between 0 and 200 inclusive, b is an integer between 0 and 50 inclusive, and if b is equal to 0, at least one of the two symbols B is A, A is a radical of formula:

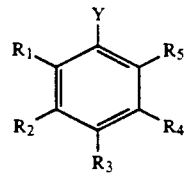

(III)

in which:

$R_1$ is hydrogen or $C_1$–$C_8$ linear or branched alkyl, $R_2$ is hydrogen, hydroxyl, $C_1$–$C_8$ linear or branched alkyl, or $C_1$–$C_8$ linear or branched alkoxy, $R_3$ is hydrogen, hydroxyl, or $C_1$–$C_8$ linear or branched alkyl, $R_4$ is hydrogen or $C_1$–$C_8$ linear or branched alkyl, $R_5$ is hydrogen, hydroxyl, or $C_1$–$C_8$ linear or branched alkoxy, at least one of the radicals $R_2$, $R_3$, and $R_5$ denoting hydroxyl, Y is a divalent radical of formula $$(O)_n\text{—}CH_2\text{—}CH(R_6)\text{—}CH_2\text{—}$$

in which:

$R_6$ is hydrogen or $C_1$–$C_4$ alkyl and n is 0 or 1, with the proviso that when n is 0, at least two of the radicals $R_1$, $R_2$, $R_3$, $R_4$, $R_5$ other than those of $R_2$, $R_3$ or $R_5$ which denote hydroxyl are different from hydrogen, or (b) the formula:

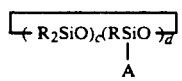

(II)

in which:

R and A have the same meanings as those shown in formula (I), c is an integer between 1 and 20 inclusive, d is an integer between 2 and 20 inclusive, and c+d is equal to or greater than 3, said antioxidant being present in an amount effective to prevent oxidation of said fatty phase of said active substance.

* * * * *